(12) United States Patent
Kushida (10) Patent No.: US 7,029,120 B2
(45) Date of Patent: Apr. 18, 2006

(54) OPHTHALMIC IMAGE PICKUP APPARATUS (75) Inventor: Akihiro Kushida, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 413 days.

(21) Appl. No.: 10/463,276

(22) Filed: Jun. 17, 2003

(65) Prior Publication Data
US 2003/0234908 A1     Dec. 25, 2003

(30) Foreign Application Priority Data
Jun. 25, 2002   (JP)  ............... 2002-184073

(51) Int. Cl.
*A61B 3/10* (2006.01)
(52) U.S. Cl. ..................... 351/211; 351/206
(58) Field of Classification Search ................ 351/206, 351/211, 205, 221
See application file for complete search history.

(56) References Cited

U.S. PATENT DOCUMENTS

| | | | | |
|---|---|---|---|---|
| 4,756,613 A | * | 7/1988 | Okashita | 351/206 |
| 6,273,565 B1 | * | 8/2001 | Matsumoto | 351/210 |
| 6,636,696 B1 | * | 10/2003 | Saito | 396/18 |
| 6,830,336 B1 | * | 12/2004 | Fransen | 351/246 |
| 2001/0056239 A1 | * | 12/2001 | Ono | 600/476 |
| 2002/0158890 A1 | * | 10/2002 | Ichikawa et al. | 345/660 |

FOREIGN PATENT DOCUMENTS

| JP | 11 235317 | 3/1999 |
|---|---|---|
| JP | 2002-065610 | 3/2002 |

* cited by examiner

*Primary Examiner*—Ali Imam
*Assistant Examiner*—John R. Sanders
(74) *Attorney, Agent, or Firm*—Morgan & Finnegan LLP (57) ABSTRACT

To provide an ophthalmic image pickup apparatus capable of setting a fixation target in a position suitable for image pickup in accordance with a selection of an image pickup purpose (group medical examination such as an adult disease examination or a glaucomatous examination). In addition, it can be determined whether operation of the fixation target is inhibited or allowed in accordance with the selected image pickup purpose.

2 Claims, 5 Drawing Sheets

OPHTHALMIC IMAGE PICKUP APPARATUS

BACKGROUND OF THE INVENTION

1. Field of the Invention

The present invention relates to an ophthalmic image pickup apparatus used in an ophthalmic doctor's office, for a group medical examination, or the like.

2. Related Background Art

Up to now, a fixation target for leading the line of sight of an eye to be examined is provided in an eye fundus image pickup apparatus. For example, there are the following settings related to the fixation target.

In eye fundus image pickup in an ophthalmic section of a hospital or the like, an image of different ophthalmic diseased regions is picked up for each patient in many cases. Accordingly, the fixation target is moved to lead the line of sight of the eye to be examined so that an image of a region which is most effective for diagnosis can be picked up. In contrast, in the case of the eye fundus image pickup in a group medical examination, it is unnecessary to move the fixation target because an image pickup region is determined according to an examination purpose.

Thus, the movement of the fixation target is made effective in the case of eye fundus image pickup in the ophthalmic section and the movement of the fixation target is made ineffective in the case of the eye fundus image pickup in the group medical examination.

Also, in the case of the eye fundus image pickup in the group medical examination, because the image pickup region is changed for each examination purpose, the position of the fixation target is changed. For example, in the case of eye fundus image pickup in an adult diseases examination, the fixation target is provided in a position in which the center between an optic disk and a macula lutea in the eye to be examined becomes the center of image.

In the case of eye fundus image pickup in a glaucomatous examination, the fixation target is provided in a position in which the optic disk of the eye to be examined becomes the center of image. In the case of eye fundus image pickup in a macular degeneration examination, the fixation target is provided in a position in which the macula lutea becomes the center of image. Thus, the fixation target is provided in the position corresponding to the purpose such as the eye fundus image pickup in the adult disease examination, the eye fundus image pickup in the glaucomatous examination, or the eye fundus image pickup in the macular degeneration examination.

However, in the above-mentioned conventional examples, there are the following problems. When the eye fundus image pickup in the ophthalmic section and the eye fundus image pickup in the group medical examination are conducted, in particular, when the purpose such as the adult disease examination, the glaucomatous examination, or the macular degeneration examination in the group medical examination is changed to conduct the eye fundus image pickup, it is necessary to reset plural settings related to the fixation target. Therefore, it takes much time and efforts for a person picking up an image and it is extremely burdensome. Further, when there is omission in settings related to the fixation target, there is a fear of causing an unexpectable operating error.

SUMMARY OF THE INVENTION

An object of the present invention is to solve the above-mentioned problems and to provide an ophthalmic image pickup apparatus in which image pickup is easy, there is no omission of its setting, and a setting related to a fixation target can be simply performed in the case where a purpose such as eye fundus image pickup in an ophthalmic section, an adult disease examination, a glaucomatous examination, or a macular degeneration examination is changed to perform eye fundus image pickup.

In order to achieve the above object, according to the present invention, there is provided an ophthalmic image pickup apparatus including: a fixation target for leading a line of sight of an eye to be examined; a purpose setting unit; a fixation target moving method storing unit for storing a moving operation method of the fixation target corresponding to a purpose set by the purpose setting unit; and a fixation target movement control unit for moving the fixation target in accordance with the moving method of the fixation target which corresponds to the purpose set by the purpose setting unit and is stored in the fixation target moving method storing unit.

Also, according to the present invention, there is provided an ophthalmic image pickup apparatus including: a fixation target for leading a line of sight of an eye to be examined; a purpose setting unit; a fixation target presenting position storing unit for storing a presenting position of the fixation target corresponding to a purpose set by the purpose setting unit; and a fixation target presenting position changing unit for presenting the fixation target in the presenting position of the fixation target which corresponds to the purpose set by the purpose setting unit and is stored in the fixation target presenting position storing unit.

Further objects and structures related to the present invention will be apparent in explanation of the embodiment below.

DESCRIPTION OF THE PREFERRED EMBODIMENTS

The present invention will be described in detail with reference to an embodiment shown in the drawings.

Figure 1:
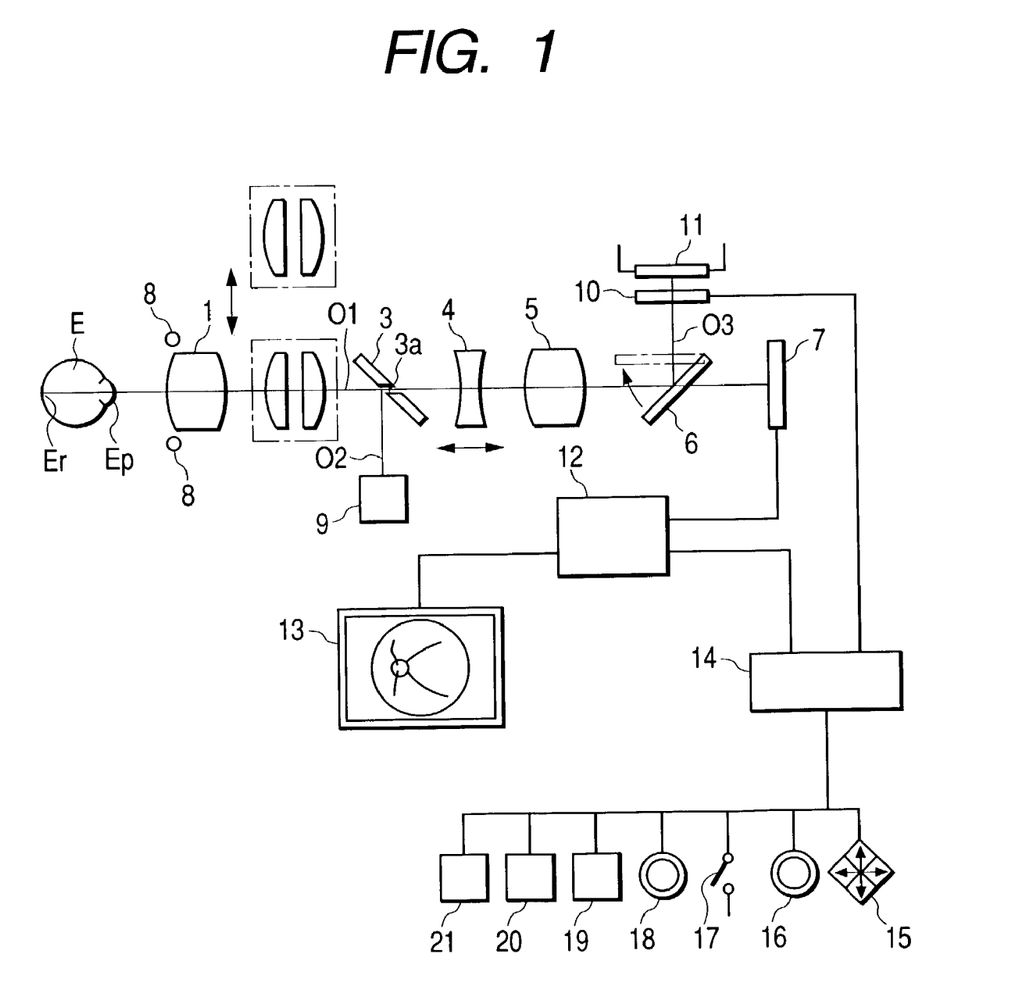
FIG. 1 is a structural view of an ophthalmic image pickup apparatus for an eye fundus.

FIG. 1 is a structural view of an ophthalmic image pickup apparatus of this embodiment. On an optical path O1 in the front of an eye to be examined E, an objective lens 1, an anterior eye part observing lens 2 which is insertable onto the optical path O1, a holed mirror 3 having an image pickup diaphragm 3a in its hole portion, a focus lens 4 which is moved along the optical path O1 to adjust a focus, an image pickup lens 5, a selection mirror 6 for reflecting a visible light and transmitting an infrared light, and an image pickup unit 7 are disposed in order. In addition, anterior eye part illuminating light sources 8 for emitting the infrared light are disposed in the vicinity of the objective lens 1.

An eye fundus illumination system 9 is disposed on an optical path O2 in the light reflecting direction of the holed mirror 3. According to the eye fundus illumination system 9, an eye fundus Er of the eye to be examined E is irradiated with the infrared light at the time of eye fundus observation and the eye fundus Er is irradiated with the visible light at the time of eye fundus image pickup. In addition, a liquid crystal display unit 10 for displaying a fixation target in a position substantially conjugate with the eye fundus Er and an illumination light source 11 for illuminating the liquid crystal display unit 10 from its rear side with the visible light are disposed on an optical path O3 in the light reflecting direction of the selection mirror 6.

Figure 2:
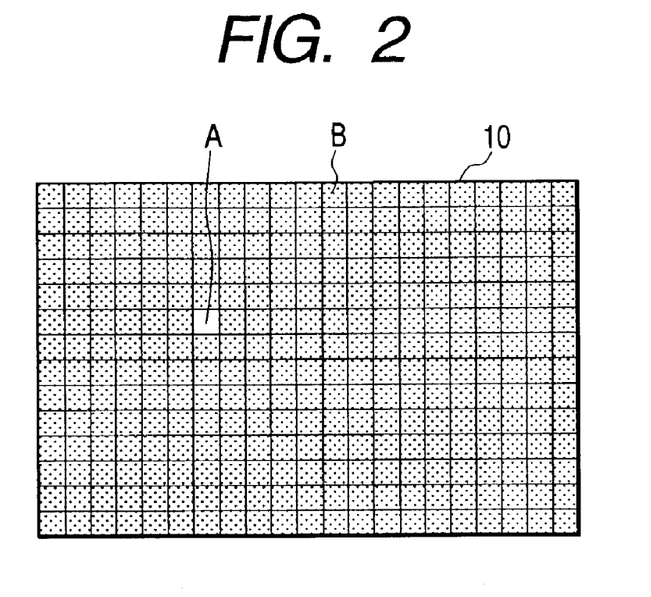
FIG. 2 is a front view of a liquid crystal display unit.

FIG. 2 is a schematic view of the liquid crystal display unit 10. In the liquid crystal display unit 10, a plurality of cells which are each made of liquid crystal and capable of setting a transmission state or a nontransmission state are arranged in matrix. When a cell in which the transmission state is set is assumed to be an opening portion "A" and a cell in which the nontransmission state is set is assumed to be a light shielding portion "B," of lights emitted from the illumination light source 11, a light transmitting through the opening portion "A" is reflected by the selection mirror 6. The reflected light passes through the image pickup lens 5, the focus lens 4, the hole portion of the holed mirror 3, and the objective lens 1 and reaches the eye fundus Er through a pupil Ep of the eye to be examined E. In other words, an image of the opening portion "A" is presented on a dark background as the fixation target for a person to be examined in which the pupil Ep is located on the optical path O1 of the objective lens 1.

An output of the image pickup unit 7 is connected with a television monitor 13 through an image control unit 12. Further, an output of the image control unit 12 is connected with a function control unit 14 for controlling the entire apparatus. The function control unit 14 is connected with the liquid crystal display unit 10, a fixation target movement operating switch 15 for controlling a presenting position of the fixation target, that is, a position of the opening portion "A" of the liquid crystal display unit 10, an anterior eye part and eye fundus selecting switch 16 for controlling whether or not the anterior eye part observing lens 2 is inserted onto the optical path O1, a right-and-left-eye selection detecting switch 17, an image pickup switch 18, a memory 19, a purpose selecting unit 20 for selecting a purpose such as eye fundus image pickup in an ophthalmic section, an adult disease examination, a glaucomatous examination, or a macular degeneration examination, and a purpose-by-purpose fixation target setting storing unit 21 for storing settings with respect to movement operation of the fixation target and a presenting position thereof according to the purpose.

The following Table 1 shows a summary of the purpose-by-purpose fixation target setting storing unit 21. In the case of the eye fundus image pickup in the ophthalmic section, the fixation target is moved to lead a line of sight of the eye to be examined E so that image pickup can be performed for a region which is most effective for diagnosis. Therefore, a movement operation of the fixation target using the fixation target movement operating switch 15 is made effective. In addition, in the case of the eye fundus image pickup in a group medical examination such as an adult disease examination, a glaucomatous examination, or a macular degeneration examination, it is unnecessary to move the fixation target because an image pickup region is determined according to a diagnostic purpose. Therefore, a setting is stored so that the movement operation of the fixation target is made ineffective.

TABLE 1

| Purpose | Fixation Target Moving Operation | Fixation Target Presenting Position (Right Eye) | Fixation Target Presenting Position (Left Eye) |
|---|---|---|---|
| Ophthalmic Section | Effective | (RX1, RY1) | (LX1, LY1) |
| Adult Disease Examination | Ineffective | (RX2, RY2) | (LX2, LY2) |
| Glaucomatous Examination | Ineffective | (RX3, RY3) | (LX3, LY3) |
| Macular Degeneration Examination | Ineffective | (RX4, RY4) | (LX4, LY4) |

A relationship between a fixation target presenting position in the liquid crystal display unit 10 and a position of a macula lutea "m" on an eye fundus image imaged onto the image pickup surface of the image pickup unit 7 is obtained from optical design values of the ophthalmic image pickup apparatus and optical data of a standard eye. From this relationship, the fixation target presenting position is set according to the purpose.

Figure 3:
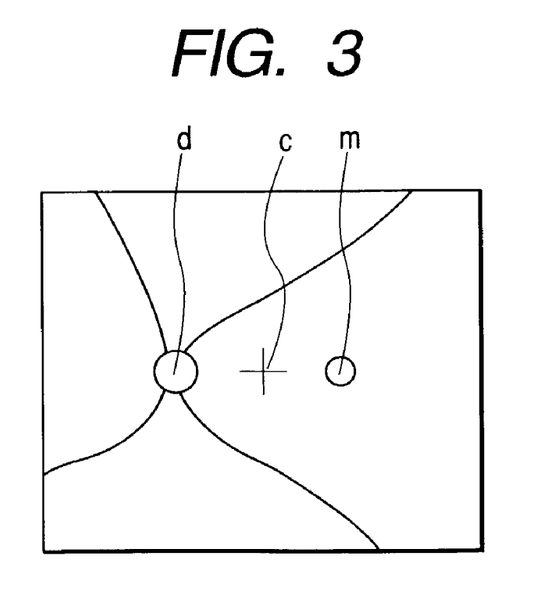
FIG. 3 is an explanatory view of eye fundus image pickup in an adult disease examination.

FIG. 3 is a schematic view of the eye fundus image pickup in the adult disease examination. In the eye fundus image pickup in the adult disease examination, in order to locate a macula lutea "m" in a position shifted from the center "c" of an image by only ½ of a distance between an optic disk "d" and the macula lutea "m" a fixation target presenting position is calculated from a relationship between the above-mentioned fixation target presenting position and the position of the macula lutea "m" on the eye fundus image. When a person to be examined gazes the fixation index presented in the calculated position, the center of image "c" becomes the center between the optic disk "d" and the macula lutea "m" in the eye to be examined E.

Figure 4:
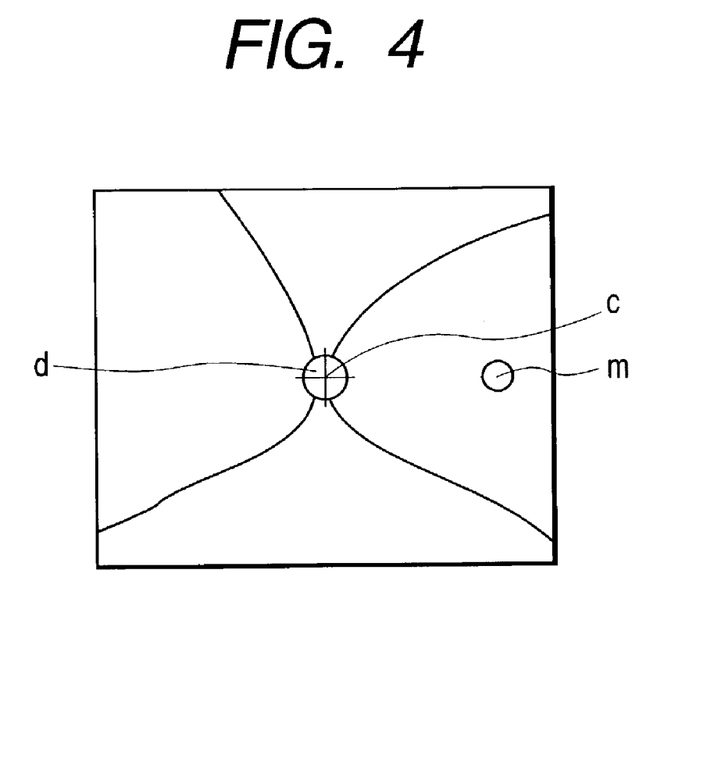
FIG. 4 is an explanatory view of eye fundus image pickup in a glaucomatous examination.

FIG. 4 is a schematic view of the eye fundus image pickup in the glaucomatous examination. According to the eye fundus image pickup in the glaucomatous examination, in order to locate the macula lutea "m" in a position shifted from the center of image "c" by only a distance between the optic disk "d" and the macula lutea "m," a fixation target presenting position is calculated from a relationship between the above-mentioned fixation target presenting position and the position of the macula lutea "m" on the eye fundus image. When the person to be examined gazes the fixation index presented in the calculated position, the optic disk "d" of the eye to be examined E becomes the center of image "c."

Figure 5:
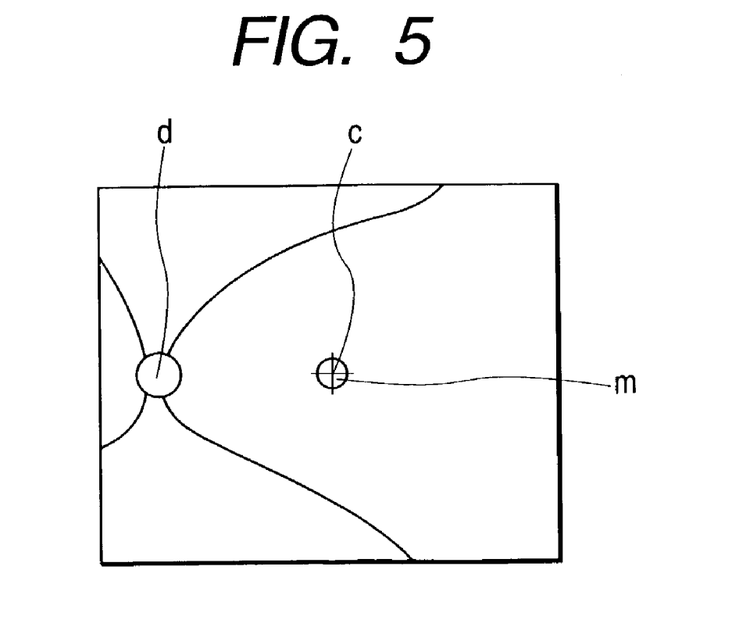
FIG. 5 is an explanatory view of eye fundus image pickup in a macular degeneration examination.

FIG. 5 is a schematic view of the eye fundus image pickup in the macular degeneration examination. In the eye fundus image pickup in the macular degeneration examination, in order to locate the macula lutea "m" in the center of image "c," a fixation target presenting position is calculated from a relationship between the above-mentioned fixation target presenting position and the position of the macula lutea "m" on the eye fundus image. When the person to be examined gazes the fixation index presented in the calculated position, the macula lutea "m" of the eye to be examined E becomes the center of image "c." Note that the fixation target presenting positions corresponding to these purposes are set and stored in the purpose-by-purpose fixation target setting storing unit 21 as shown in Table 1.

Thus, the fixation target presenting position is set for each of the right eye and the left eye. Note that the fixation target presenting position for the eye fundus image pickup in the ophthalmic section may be set an arbitrary position because it is assumed to move the fixation target.

In the ophthalmic image pickup apparatus having such a structure, a procedure in the case where an eye fundus image is picked up by a person picking up an image will be described with reference to a flow chart shown in FIG. 6. First, a power source switch (not shown) is operated to start the operation of an ophthalmic image pickup apparatus main body. In step S1, an intended purpose such as the eye fundus image pickup in the ophthalmic section, the eye fundus image pickup in the adult disease examination, the eye fundus image pickup in the glaucomatous examination, or the eye fundus image pickup in the macular degeneration examination is selected by the person picking up the image. In addition, the selected purpose is stored in the memory 19.

After the completion of the purpose selection in step S1, an anterior eye part is observed in step S2. In a state in which the anterior eye part is observed, the anterior eye part observing lens 2 is inserted onto the optical path O1 and the selection mirror 6 is located on the optical path O1. With this state, an anterior eye part image resulting from the illumination with an infrared light emitted from the anterior eye part illuminating light sources 8 is passed through the objective lens 1, the anterior eye part observing lens 2, the hole portion of the holed mirror 3, the focus lens 4, and the image pickup lens 5. The anterior eye part image is imaged onto the image pickup surface of the image pickup unit 7, converted into a video signal, and displayed on the television monitor 13 through the image control unit 12.

While viewing the picture displayed on the television monitor 13, the person picking up the image operates an operation stick (not shown). When alignment with an eye to be picked up, for example, the right eye is completed, the function control unit 14 determines that the alignment with the right eye is completed in accordance with the output of the right-and-left-eye selection detecting switch 17.

Figure 7:
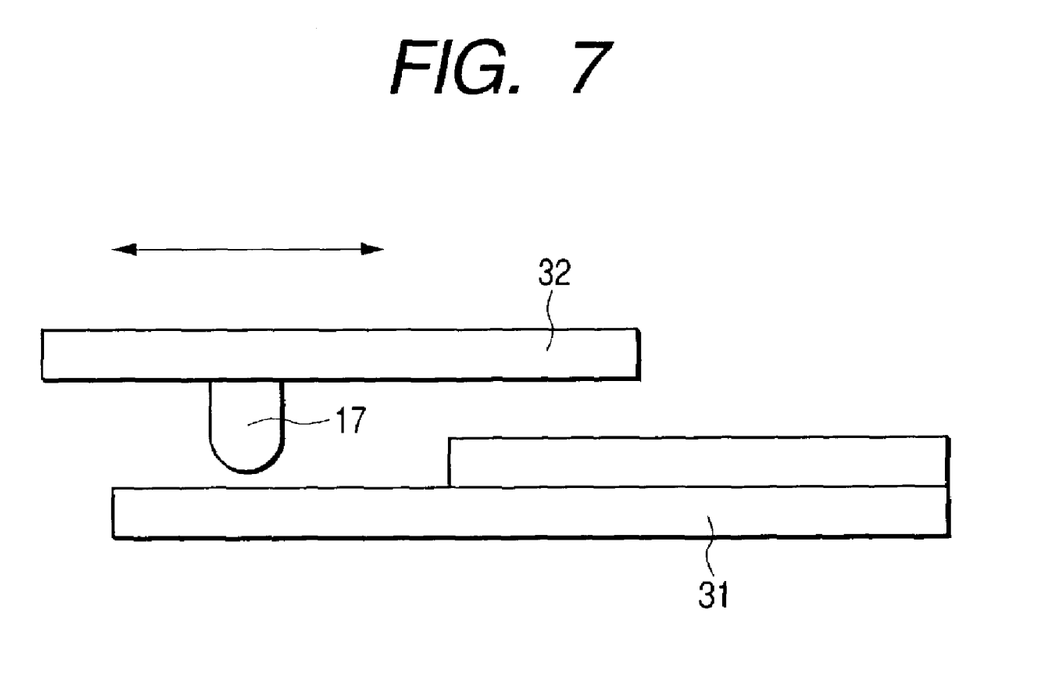
FIG. 7 is an explanatory view of a right-and-left-eye selection detecting switch.

FIG. 7 is an explanatory view of the right-and-left-eye selection detecting switch 17. A stage 32 is located above a base 31 and the right-and-left-eye selection detecting switch 17 is fixed onto the lower surface of the stage 32. The stage 32 is constructed such that it is moved in the lateral direction indicated by an arrow in the figure.

When the stage 32 is moved in the lateral direction, an on/off of the right-and-left-eye selection detecting switch 17 is switched.

After the alignments with the right eye is completed and anterior eye part and eye fundus selecting switch 16 is operated, processing is transferred to an eye fundus observation in step S3. In this eye fundus observation state, the anterior eye part illuminating light sources 8 are turned off, the anterior eye part observing lens 2 is left for the outside of the optical path O1, the selection mirror 6 is located on the optical path O1, and an infrared light is emitted from the eye fundus illumination system 9.

The infrared light emitted from the eye fundus illumination system 9 is reflected on a mirror portion of the circumference of the holed mirror 3 to illuminate a region from the pupil Ep to the eye fundus Er through the objective lens 1. An eye fundus image resulting from the illumination is passed through the pupil Ep, the objective lens 1, the hole portion of the holed mirror 3, the focus lens 4, the image pickup lens 5 and the selection mirror 6. The eye fundus image is imaged onto the image pickup surface of the image pickup unit 7 and converted into a video signal, and then displayed on the television monitor 13 through the image control unit 12. In addition, in this eye fundus observation state, the fixation target is presented in the fixation target presenting position stored in the purpose-by-purpose fixation target setting storing unit 21 in accordance with the aligned eye of the right and left eyes and the purpose selected in step S1.

Subsequently, when the eye fundus image pickup in the ophthalmic section is selected as the purpose in step S4, the processing goes to step S5. A fixation target presenting position for right eye (RX1, RY1) which is used for the eye fundus image pickup in the ophthalmic section and stored in the purpose-by-purpose fixation target setting storing unit 21 is set as the opening portion "A" of the liquid crystal display unit 10. Other regions are set as the light shielding portions "B." Then, the illumination light source 11 is turned on to present the fixation target, thereby leading the eye to be examined E.

Also, when the eye fundus image pickup in the adult disease examination is selected as the purpose, the processing goes to step S6. A fixation target presenting position for right eye (RX2, RY2) which is used for the eye fundus image pickup in the adult disease examination and stored in the purpose-by-purpose fixation target setting storing unit 21 is set as the opening portion "A" of the liquid crystal display unit 10. Other regions are set as the light shielding portions "B." Then, the illumination light source 11 is turned on to present the fixation target, thereby leading the eye to be examined E.

Figure 6:
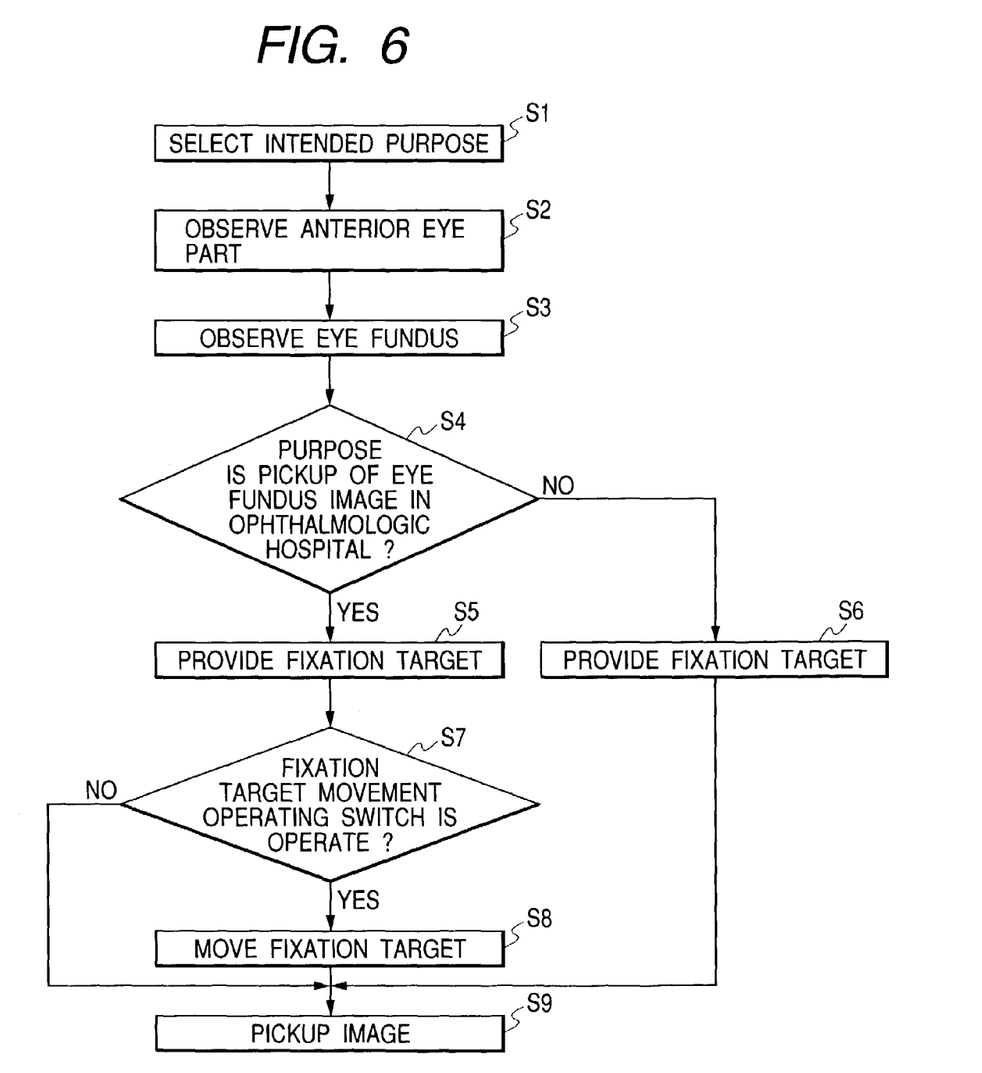
FIG. 6 is a flow chart for eye fundus image pickup.

Note that descriptions with respect to the eye fundus image pickup in the glaucomatous examination and the eye fundus image pickup in the macular degeneration examination are omitted in the flow chart shown in FIG. 6. However, as in the case of adult disease examination, a fixation target presenting position (right eye) for a corresponding purpose which is stored in the purpose-by-purpose fixation target setting storing unit 21 is set as the opening portion "A" of the liquid crystal display unit 10. Other regions are set as the light shielding portions "B." Then, the illumination light source 11 is turned on to present the fixation target. In this eye fundus observation state, a precision alignment between a main body optical system and the eye fundus Er of the eye to be examined E with respect to longitudinal and lateral positions and a working is distance is conducted by the operation stick (not shown). In addition, the focus lens 4 is moved along the optical path O1 to make, focusing.

In the case where the eye fundus image pickup in the ophthalmic section is selected as the purpose, when the fixation target movement operating switch 15 is operated in step S7, the opening portion of the liquid crystal display unit 10 is moved in step S8 to move the fixation target, thereby leading the line of sight of the eye to be examined E. On the other hand, when the eye fundus image pickup in the adult disease examination is selected as the purpose, the fixation target presenting position is fixed. Therefore, the operation of the fixation target movement operating switch 15 is made ineffective.

With respect to the eye fundus image pickup in the glaucomatous examination and the eye fundus image pickup in the macular degeneration examination, the operation of the fixation target movement operating switch 15 is made ineffective as in the case of adult disease examination Then, the line of sight of the eye to be examined E is led to the fixed fixation target presenting position.

When the precision alignment, focusing, and the leading of the eye to be examined E are completed, the eye fundus image pickup is performed by operating the image pickup switch 18 in step S9. When the person picking up the image operates the image pickup switch 18, the selection mirror 6 is left for the outside of the optical path O1 and the image pickup unit 7 starts optical storage for still image pickup. In addition, the eye fundus illumination system 9 emits a visible light, so that the eye fundus Er of the eye to be examined E is illuminated with the visible light as in the above-mentioned case of the infrared light. An eye fundus image thus illuminated is passed along the same path as in the above-mentioned case of the infrared light and imaged onto the image pickup unit 7. The still image is converted into digital data by the image control unit 12, stored in an image memory of the image control unit 12, and displayed on the television monitor 13.

Note that, in this embodiment, only one cell of the liquid crystal display unit 10 is set as the opening portion "A" to present the fixation target. A plurality of cells may be set as the opening portion "A" to present the fixation target. Further, when a plurality of cells may be set as the opening portion "A," a fixation target with an arbitrary shape can be presented.

Also, in this embodiment, the fixation target is presented and moved using the liquid crystal display unit 10 and the illumination light source 11. The fixation target can be presented and moved by a fixation target light source composed of an LED, a motor for controlling a position of the fixation target light source, and the like.

Further, immediately after the power source is turned on, the purpose such as the eye fundus image pickup in the ophthalmic section, the eye fundus image pickup in the adult disease examination, the eye fundus image pickup in the glaucomatous examination, or the eye fundus image pickup in the macular degeneration examination is selected by the purpose selecting unit 20. However, the purpose may be selected except for a time point immediately after the power source is turned on.

Note that in the case where a nonvolatile memory is used as the memory 19 and the selected purpose is stored in the nonvolatile memory, when the power source which is operated to start the operation of the main body, settings with respect to the movement operation of the fixation target for the previous selected purpose and the presenting position thereof can be conducted without selecting the purpose.

Most of the above-mentioned processings can be realized by programs. Therefore, even when a recording medium in which program codes of a software for realizing functions of the above-mentioned embodiment are recorded is supplied to a system or an apparatus and a computer (CPU or MPU) in the system or the apparatus reads the program codes stored in the recording medium and executes them, the present invention can be realized as a matter of course.

In this case, the functions of the above-mentioned embodiment are realized by the program codes themselves read from the recording medium. The recording medium in which the program codes are recorded constructs the present invention. A floppy disk, a hard disk, an optical disk, a magneto-optical disk, a CD-ROM, a magnetic tape, a nonvolatile memory card, a ROM, or the like can be used as the recording medium for providing the program codes.

In this embodiment, the eye fundus camera is described and a slit lamp can be similarly constructed.

As described above, in the ophthalmic image pickup apparatus according to the present invention, there are provided the purpose selecting unit for selecting the purpose such as the eye fundus image pickup in the ophthalmic section, the eye fundus image pickup in the adult disease examination, the eye fundus image pickup in the glaucomatous examination, or the eye fundus image pickup in the macular degeneration examination and the purpose-by-purpose fixation target setting storing unit for storing settings with respect to the movement operation of the fixation target and the presenting position thereof in accordance with the purpose. Therefore, when the purpose is changed to perform the eye fundus image, settings with respect to the movement operation of the fixation target, the presenting position thereof, and the like can be conducted only by selecting the purpose. Thus, it is unnecessary to change plural settings with respect to the movement operation of the fixation target and the presenting position thereof, so that the settings can be easily changed in a short time.

What is claimed is:

1. An ophthalmic image pickup apparatus comprising:
   a fixation target for leading a line of sight of an eye to be examined;
   purpose setting means for setting an image pickup purpose of the ophthalmic image pickup apparatus;
   fixation target moving method storing means for storing a moving method of the fixation target corresponding to the image pickup purpose set by the purpose setting means;
   fixation target movement control means for controlling a movement of the fixation target; and
   manual operation means for manually operating the movement of the fixation target,
   wherein the fixation target movement control means
      controls the movement of the fixation target in accordance with the moving method of the fixation target which corresponds to the set image pickup purpose and is stored in the fixation target moving method storing means: and
      makes operation of the manual operation means effective or ineffective in accordance with the set image pickup purpose.

2. An ophthalmic image pickup apparatus comprising:
   a fixation target for leading a line of sight of an eye to be examined;
   purpose setting means for setting an image pickup purpose of the ophthalmic image pickup apparatus;
   fixation target setting position storing means for storing a setting position of the fixation target corresponding to the image pickup purpose set by the purpose setting means;
   fixation target movement control means for controlling a movement of the fixation target; and
   manual operation means for manually operating the movement of the fixation target;
   wherein the fixation target movement control means
      controls the movement of the fixation target in accordance with the setting position of the fixation target which corresponds to the set image pickup purpose and is stored in the fixation target setting position storing means; and
      makes operation of the manual operation means effective or ineffective in accordance with the set image pickup purpose.

* * * * *

UNITED STATES PATENT AND TRADEMARK OFFICE
CERTIFICATE OF CORRECTION

PATENT NO. : 7,029,120 B2
APPLICATION NO. : 10/463276
DATED : April 18, 2006
INVENTOR(S) : Akihiro Kushida It is certified that error appears in the above-identified patent and that said Letters Patent is hereby corrected as shown below:

Column 6,
Line 42, delete "is" (first occurrence).
Line 60, add -- . -- after "examination".

Signed and Sealed this

Fourth Day of July, 2006

JON W. DUDAS
*Director of the United States Patent and Trademark Office*